United States Patent [19]

Summerford

[11] Patent Number: 4,970,341
[45] Date of Patent: Nov. 13, 1990

[54] AMINE OXIDE PROCESS

[75] Inventor: Teresa K. Summerford, Baton Rouge, La.

[73] Assignee: Ethyl Corporation, Richmond, Va.

[21] Appl. No.: 17,854

[22] Filed: Feb. 24, 1987

[51] Int. Cl.$^5$ ............................................ C07C 291/00
[52] U.S. Cl. .................................... 564/298; 546/184
[58] Field of Search ................ 564/298, 297; 546/184

[56] References Cited

U.S. PATENT DOCUMENTS

| 2,169,976 | 8/1939 | Guenther et al. | 564/298 X |
| 3,047,579 | 7/1962 | Witman | 564/297 X |
| 3,388,069 | 6/1968 | Lindner et al. | 564/298 X |
| 3,402,128 | 9/1968 | Puchta et al. | 564/297 X |

Primary Examiner—Robert V. Hines
Attorney, Agent, or Firm—Joseph D. Odenweller; John F. Sieberth

[57] ABSTRACT

A process for accelerating the oxidation of tert-amines by hydrogen peroxide by conducting the reaction in the presence of an ascorbic acid promoter.

21 Claims, No Drawings

AMINE OXIDE PROCESS

BACKGROUND OF THE INVENTION

1. Field of the Invention

The present invention is directed to the preparation of amine oxides. More particularly, this invention involves the use of ascorbic acid as a catalyst for accelerating the oxidation of amines by reaction with hydrogen peroxide ($H_2O_2$) to form amine oxides.

2. Background

Oxidation of a tertiary amine such as didecylmethylamine by reaction with hydrogen peroxide to form a tert-amine oxide is known. This reaction is illustrated by the following equation.

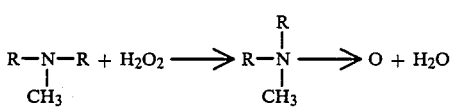

An object of the present invention is to increase the oxidation reaction rate.

Another object of this invention is to provide a process that yields clarified tert-amine oxides.

SUMMARY OF THE INVENTION

Accordingly, this invention provides a process for accelerating the oxidation of tert-amines by aqueous hydrogen peroxide by conducting the reaction in the presence of a promoter amount of ascorbic acid. In addition to catalyzing the reaction, ascorbic acid acts as a stabilizer and clarifier of the amine oxide product.

DESCRIPTION OF THE PREFERRED EMBODIMENTS

A preferred embodiment of this invention is a process for oxidizing a tert-amine by reaction with hydrogen peroxide to form a tert-amine oxide, said process comprising contacting said tert-amine with aqueous hydrogen peroxide in the presence of a promoter amount of ascorbic acid whereby the reaction rate is increased. The reactants involved in this process are tert-amines and aqueous hydrogen peroxide. The tert-amines include but are not limited to any amine in which the amino nitrogen atom is bonded to 2 or 3 carbon atoms and no hydrogen atoms. Examples of these are:
trimethylamine
triethylamine
tridecylamine
tridodecylamine
trieicosylamine
docosyldioctylamine
triacontyldibutylamine
N,N-dimethylaniline
N-methyldiphenylamine
triphenylamine
N-methyl-N-dodecylaniline pyridine
2-methylpyridine
N,N-dimethylpiperazine
N-ethylpiperidine
and the like.

The preferred amines are the tri-alkyl amines in which the alkyls are straight or branched chain and contain 1 to about carbon atoms such as:
trimethylamine
triethylamine
trioctylamine
tridodecylamine
2-ethylhexyl di-n-propylamine
isopropyl di-n-dodecylamine
isobutyl di-n-eicosylamine
2-methyldocosyl di-(2-ethylhexyl) amine
triacontyl di-(2-butyldecyl) amine
and the like.

A more preferred embodiment of the tri-alkyl amine is a primary tri-alkyl amine having the structure

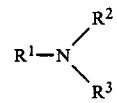

wherein $R^1$, $R^2$ and $R^3$ are primary alkyls having 1-30 carbon atoms. Representative examples include but are not limited to
trimethylamine
tri-n-pentylamine
tri-n-dodecylamine
n-octadecyl di-(n-butyl)amine
n-eicosyl di-(n-decyl)amine
n-triacontyl n-dodecylmethylamine
and the like.

A still more preferred embodiment of the amine reactants are the tri-primary alkyl amines of formula I wherein $R^1$ is a primary alkyl having about 8-20 carbon atoms, $R^2$ is a primary alkyl having either 1-2 carbon atoms or having 8-20 carbon atoms and $R^3$ is methyl or ethyl. Representative examples of these are
n-octyldimethylamine
n-decyldiethylamine
n-dodecyldiethylamine
n-octadecyldimethylamine
n-eicosyl dimethylamine
n-octyl n-dodecylmethylamine
n-decyl n-eicosylethylamine
and the like.

A highly preferred class of tert-amines are those having the structures:

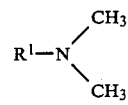

and

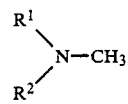

where $R^1$ and $R^2$ are primary alkyls containing 8-20 carbon atoms.

Representative examples of these are
n-octyldimethylamine
n-decyldimethylamine
n-dodecyldimethylamine
n-tetradecyldimethylamine
n-hexadecyldimethylamine
n-octadecyldimethylamine
n-eicosyldimethylamine
di-(n-octyl)methylamine
di-(n-decyl)methylamine
di-(n-dodecyl)methylamine di-(n-tetradecyl)methylamine
di-(n-hexadecyl)methylamine
di-(n-octadecyl)methylamine
di-(n-eicosyl)methylamine
n-octyl n-dodecylmethylamine
n-decyl n-octadecylmethylamine
and the like.

Of course even these highly preferred amines can contain minor amounts of other tert-amines including all those previously mentioned.

The second reactant, aqueous hydrogen peroxide, is used at a concentration between 3 and 99 wt. %. The preferred embodiment uses 30–70 wt. % hydrogen peroxide with the most preferred embodiment being about 50 wt. %.

Stoichiometry requires one mole of hydrogen peroxide to be reacted with one mole of tert-amine. A preferred amount of hydrogen peroxide is about 0.9 to 2.5 moles. A more preferred amount of hydrogen peroxide is 1.0 to 1.5 moles with a still more preferred amount being 1.05 to 1.3 moles. The most preferred quantity of hydrogen peroxide is 1.1 to 1.25 moles.

The mode of adding the reactants is variable. The amine can be added to the hydrogen peroxide or vice-versa. Another mode is to co-mingle reactants as with an in-line mixing arrangement. The preferred embodiment would be to add the hydrogen peroxide at a controlled rate to the amine. By controlled rate it is meant to add the hydrogen peroxide as it reacts rather than all at once so that the amount of $H_2O_2$ in the reaction mixture does not reach a hazardous level.

However, the reactants are mixed following a nitrogen sparge utilizing a sparge tube submerged in the amine. A nitrogen pad may be placed on top of a reflux condenser and the amine heated to around 65.C. The ascorbic acid may be added to the amine either after the sparge and before heating or following the removal of the nitrogen pad after heating. The amine may be heated to 80.C., but care must be exercised at 85° C.–90° C. when olefin formation could initiate to some extent.

A useful quantity of ascorbic acid should be a promoter amount between 0.001 and 10 wt. percent. A preferred range is between 0.001 and 3 wt. percent with excellent results obtained between 0.001 and 1 wt. percent.

The reaction is conducted at a temperature high enough to cause the desired reaction to proceed but not so high as to cause excessive decomposition of the reactants or products. A useful temperature range is 30° C. to 200° C. A preferred range is 40° C. to 150° C. with a more preferred range of 45° C. to 100° C. Excellent results are obtained around 65° C.

The reaction should be conducted for a time sufficient to achieve the desired degree of completion of the reaction. A feature of the present process is that it achieves a higher reaction rate than that achieved under the same conditions but without the ascorbic acid promoter. Good results can be obtained in 0 to 48 hours with the more preferable range being between 10 to 36 hours and the most preferable being 20 to 28 hours. The reaction mixture results in amine oxide in water.

A further benefit of the present process is that it prevents the formation of color in the oxide thereby giving a more marketable product. The reaction normally involves the use of hydrogen peroxide as shown by the following equation.

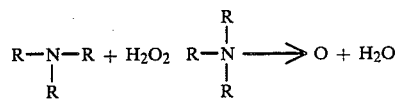

wherein R can be the same or different group, preferably a hydrocarbon group or the R groups can form a ring as in pyridine or piperidine.

The following example illustrates the oxidation process according to the present invention and in no manner is it intended to limit the invention described.

EXAMPLE 1

Comparative Example

In a 2 liter reaction flask was placed 500.03 g of di-(n-decyl) methylamine. While stirring under a $N_2$ atmosphere at about 65° C. a total of 131.68 g of 50 wt % aqueous hydrogen peroxide was added over a 1 hour period. The temperature was then raised to 75° C. and stirring continued for 23 hours. The reaction mixture was then cooled. The results are shown in Table I.

EXAMPLE 2

The Present Invention

In a reaction flask was placed 500 g of di-(n-decyl) methylamine to which was added 5 g of ascorbic acid promoter. A positive nitrogen flow was placed over the mixture and heated to 65° C. Then 131.64 g of 50 wt % aqueous hydrogen peroxide was then added over a 1 hour period while stirring. The temperature was then raised to 75° C. And stirring continued for another 23 hours. After one and six hours at 75° C. the amine conversion rate was increased by about 30% and 15% respectively. The reaction mixture was then cooled. The results are shown in the following Table I.

TABLE I

|  | Example # | |
|---|---|---|
|  | 1 | 2 |
| Reaction Parameters | | |
| Catalyst | None | Ascorbic Acid |
| Temperature (°C.) | | |
| Addition | 65 | 65 |
| Hold | 75 | 75 |
| Time (Hours) | | |
| Addition | 1 | 1 |
| Hold | 23 | 23 |
| Percent Amine Conversion Over Time (NMR) | | |
| 1 hour | 32.9 | 62.6 |
| 3 hours | 67.4 | 91.6 |
| 6 hours | 79.2 | 96.6 |
| 24 hours | 91.4 | 97.1 |
| Final Product Analyses | | |
| % Amine Oxide (Titration) | 69.3 | 77.75 |
| % Free Amine (GC) | 9.6 | 2.7 |
| % $H_2O_2$ (Titration) | .29 | .27 |
| % Olefin (NMR) | .8 | 1.3 |
| Color (APHA) | 150 | 10–20 |

AScorbic acid acts as a stabilizer and clarifier to the oxidation reaction. Additionally, its safety is demonstrated by use as a nitrosamine inhibitor and whitening agent in cosmetic formulation.

I claim:

1. A process for oxidizing a tert-amine by reaction with hydrogen peroxide to form a tert-amine oxide, said process comprising contacting said tert-amine with aqueous hydrogen peroxide in the presence of a promoter amount of ascorbic acid whereby the reaction rate is increased.

2. A process of claim 1 wherein said tert-amine is a tri-alkyl amine.

3. A process of claim 2 wherein said alkyl is a primary alkyl.

4. A process of claim 3 wherein said tri-primary alkyl amine has the structure.

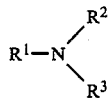

wherein $R^1$, $R^2$ and $R^3$ are primary alkyls having 1–30 carbon atoms.

5. A process of claim 4 wherein $R^1$ is a primary alkyl having about 8–20 carbon atoms, $R^2$ is a primary alkyl having 1–2 carbon atoms or having 8–20 carbon atoms and $R^3$ is methyl or ethyl.

6. A process of claim 5 wherein said tert-amine has the structure

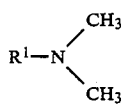

7. A process of claim 5 wherein said tert-amine has the structure

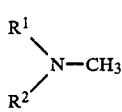

wherein $R^2$ is a primary alkyl having about 8–20 carbon atoms.

8. A process of claim 1 wherein said aqueous hydrogen peroxide contains about 20–90 wt. % $H_2O_2$.

9. A process of claim 8 wherein said aqueous hydrogen peroxide contains about 30–70 wt. % $H_2O_2$.

10. A process of claim 9 wherein said tert-amine is a tri-alkyl amine.

11. A process of claim 10 wherein said alkyl is a primary alkyl.

12. A process of claim 11 wherein said tri-primary alkyl amine has the structure

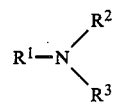

wherein $R^1$, $R^2$ and $R^3$ are primary alkyls having 1–30 carbon atoms.

13. A process of claim 12 wherein $R^1$ is a primary alkyl having about 8–20 carbon atoms, $R^2$ is a primary alkyl 1–2 carbon atoms or having 8–20 carbon atoms and $R^3$ is methyl or ethyl.

14. A process of claim 13 wherein said tert-amine has the structure

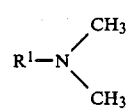

15. A process of claim 14 wherein said tert-amine has the structure

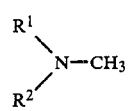

wherein $R^2$ is a primary alkyl having about 8–20 carbon atoms.

16. A process of claim 13 wherein said tert-amine is a $C_{8-20}$ primary alkyl dimethyl amine.

17. A process of claim 16 wherein said tert-amine is decyl dimethylamine.

18. A process of claim 16 wherein said tert-amine is dodecyl dimethyl amine.

19. A process of claim 13 wherein said tert-amine is a di-$C_{8-20}$ primary alkyl methylamine.

20. A process of claim 19 wherein said tert-amine is didecyl methylamine.

21. A process of claim 19 wherein said tert-amine is didodecyl methylamine.

* * * * *